US006925392B2

(12) United States Patent
McNeil, III et al.

(10) Patent No.: US 6,925,392 B2
(45) Date of Patent: Aug. 2, 2005

(54) METHOD FOR MEASURING FLUID CHEMISTRY IN DRILLING AND PRODUCTION OPERATIONS

(75) Inventors: Robert Irving McNeil, III, Cypress, TX (US); Sabine Claudia Zeilinger, Houston, TX (US); James William Nicholson, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/644,390

(22) Filed: Aug. 20, 2003

(65) Prior Publication Data

US 2004/0098202 A1 May 20, 2004

Related U.S. Application Data
(60) Provisional application No. 60/404,899, filed on Aug. 21, 2002.

(51) Int. Cl.$^7$ ............................................. G06F 19/00
(52) U.S. Cl. ........................... 702/22; 702/11; 702/12; 702/23
(58) Field of Search ...................... 435/28–29; 702/9, 702/11, 12, 22, 23, 24, 25, 27, 100, 108, 186, 188; 422/100, 101, 102; 210/198.2, 656

(56) References Cited

U.S. PATENT DOCUMENTS

| | | | | |
|---|---|---|---|---|
| 5,049,673 A | | 9/1991 | Tsien et al. ................... 546/107 |
| 5,165,292 A | * | 11/1992 | Prohaska ....................... 73/866 |
| 5,244,636 A | | 9/1993 | Walt et al. ................ 422/82.07 |
| 5,250,264 A | | 10/1993 | Walt et al. ................ 422/82.07 |
| 5,304,487 A | | 4/1994 | Wilding et al. ................ 435/29 |
| 5,376,252 A | | 12/1994 | Ekstrom et al. ............. 204/603 |
| 5,501,980 A | * | 3/1996 | Katerinopoulos et al. ..... 436/74 |
| 5,502,560 A | | 3/1996 | Anderson et al. ............ 356/128 |
| 5,610,708 A | | 3/1997 | Anderson et al. ............ 356/128 |
| 5,760,479 A | | 6/1998 | Yang et al. ................... 257/778 |
| 5,779,868 A | | 7/1998 | Parce et al. ................. 204/604 |
| 5,800,690 A | | 9/1998 | Chow et al. ................. 204/451 |
| 5,800,890 A | * | 9/1998 | Myers ....................... 428/41.7 |
| 5,876,675 A | | 3/1999 | Kennedy ...................... 422/99 |
| 5,942,443 A | | 8/1999 | Parce et al. ................. 436/514 |
| 5,984,023 A | | 11/1999 | Sharma et al. ................ 175/50 |
| 6,046,056 A | | 4/2000 | Parce et al. .............. 204/403.5 |
| 6,117,396 A | * | 9/2000 | Demers ....................... 422/100 |
| 6,132,685 A | | 10/2000 | Kercso et al. ............... 422/104 |
| 6,150,119 A | | 11/2000 | Kopf-Sill et al. ............ 435/7.1 |
| 6,150,180 A | | 11/2000 | Parce et al. ................. 436/514 |
| 6,171,067 B1 | | 1/2001 | Parce .......................... 417/48 |
| 6,176,323 B1 | * | 1/2001 | Weirich et al. ................ 175/40 |
| 6,265,179 B1 | | 7/2001 | Zhou et al. ................... 435/28 |
| 6,267,858 B1 | | 7/2001 | Parce et al. ................. 204/600 |
| 6,274,337 B1 | | 8/2001 | Parce et al. .................. 435/29 |
| 6,306,659 B1 | | 10/2001 | Parce et al. ................... 436/47 |
| 6,358,387 B1 | | 3/2002 | Kopf-Sill et al. ........... 204/603 |
| 6,387,290 B1 | | 5/2002 | Brody et al. ................... 216/99 |

FOREIGN PATENT DOCUMENTS

WO           96/04547         2/1996        G01N/27/00

OTHER PUBLICATIONS

George M. Whitesides amd Abraham D. Stroock, "Flexible Methods for Microfluidics", Physics Today Online, pp. 1–8.
International Search Report dated Aug. 19, 2003.

* cited by examiner

Primary Examiner—Bryan Bui (57) ABSTRACT

A method for chemical analysis of fluids utilized in hydrocarbon exploration and production in which microfluidic systems designed to react to specific characteristics of a fluid are introduced into fluid samples or during operations. The microfluidic systems are then recovered and subjected to analysis to permit one to measure the desired characteristics.

47 Claims, 5 Drawing Sheets

METHOD FOR MEASURING FLUID CHEMISTRY IN DRILLING AND PRODUCTION OPERATIONS

This application claims the benefit of U.S. Provisional Application No. 60/404,899 filed Aug. 21, 2002, the entire disclosure of which is hereby incorporated by reference

FIELD OF THE INVENTION

This invention relates to the measurement and analysis of drilling-, drill-in, completion-, production- and formation fluids on the well site or in a remote laboratory. More particularly it relates to microfluidic (i.e. micro-electronic machines type or MEMS) technology, measuring drilling-, drill-in, completion-, formation and production fluids in real-time, on-site or remote, faster, more reliably and more economically, with better reproducibility of results. Examples of fluid properties that can be measured with the proposed method include, for example, measurements of ion concentration in the fluids such as chloride concentration, water hardness ($Ca^{2+}$, $Mg^{2+}$), bromide ion concentration, heavy metals such as Zn, Ba, and Cd, shale reactivities, zeta potential, enzymes, and biopolymers.

Based on these tests a drilling or completion fluid can be optimized for better performance, higher standards of environmental compliance, and better economical and technical performance, and timely intervention can be accomplished to minimize damage resulting from incompatibilities in completion and production fluids.

BACKGROUND OF THE INVENTION

In the process of drilling a well, solids, fluids, and gases are brought to the surface by the drilling fluid (mud) and are collected and analyzed. Drilling, drill-in, and completion fluids are typically analyzed several times a day for several key-chemical properties to ensure the technical, environmental and safe performance of the drilling fluid. Examples of properties tested in drilling, completion, and production fluids are: alkalinity, chloride content, polymer concentration, density, hardness, iron content, methylene blue test, pH, potassium content, silicate concentration, sulfide concentration, salinity, shale inhibitor content, hydrate inhibitor content, asphaltene precipitation inhibitor content, heavy metal concentration, and compatibility of formation fluid with the completion fluid.

Typically, these tests are one or two daily measurements of the fluid with simplistic, yet relatively time-consuming analytical tests. On occasion a more detailed analysis is performed. Considering the complexity of the fluid systems, the high cost of drilling and completing a well, and the danger of production losses, such tests are not entirely satisfactory analytical tools. It would be desirable if there were a method available to analyze chemical properties of drilling mud, completion fluid or production fluid that was faster, more flexible, and provided a higher reproducibility of data.

Chemical sensor techniques and especially micro-electrical machines (MEMs) that measure biochemical properties are being developed in the biomedical industry. Some of the measurement techniques incorporated in these measurement devices may include, for example, optical spectroscopy (UV, visible, infrared, and near infrared), potentiometer, calorimeter, selective chemical sensors, optical rotation, diffusion, and chromatography.

The measurement principles for chemical sensors and chemical sensing devices for liquids and gases are in some cases similar, but the applications are generally very different due to the great differences in complexity and variability of the target species. Thus, gas measurements involve chemically very simple species that typically do not interact significantly with each other, either in the gas phase or in the analytical system. In contrast, liquids, especially those associated with drilling-, completing and producing wells, contain complex mixtures of solids, ionic species, surface-active agents of a variety of types, hydrocarbons, water, and polymers. Those knowledgeable in the art will recognize that not all of the techniques mentioned above are appropriate for both gases and liquids and that, even when the principles are similar, application of the techniques is very different.

U.S. Pat. No. 5,306,909 discloses a method of analyzing drilling muds that involves the use of reflectance infrared spectroscopy. The method utilizes standards of mud components for calibration and provides estimates of the concentrations of various polymers in water- and oil-based muds, water, water chemical activity, and quartz and other minerals in oil-based muds within accuracy of 10–20%. The authors claim the ability to estimate values for a variety of mud properties through use of calibration with muds for which these properties are known. Important points to note are that the method relies on a calibration set of well-characterized materials, which may or may not correspond to materials in field use, and has very limited accuracy for the mineralogy estimates, with no indication of the accuracy of the other estimates. In addition, while the method is claimed to require no sample preparation, the importance of scattering limits the particle size distribution in the samples to be analyzed. Thus, it is asserted that adaptation to an on-line application would be limited.

U.S. Pat. No. 6,176,323 discloses a method of analyzing the chemistry of drilling fluids, as well as the concentrations of tracers in these fluids. Specifically, the patent claims the ability to measure: "(a) presence of a hydrocarbon of interest in the drilling fluid, (b) presence of water in the drilling fluid, (c) amount of solids in the drilling fluid, (d) density of the drilling fluid, (e) composition of the drilling fluid downhole, (f) pH of the drilling fluid, and (g) presence of $H_2S$ in the drilling fluid". These measurements are obtained using optical spectroscopy alone, total reflectance alone, and optical spectroscopy combined with sol/gel technology to provide a medium for reactions of chemicals in the mud with chemicals in the glass to provide color centers that can be detected optically. The chemicals in the mud can be added as part of the mud program or can be present as the result of influx from the formations being drilled.

The total reflectance system requires the use of two separate detectors, one for the incoming mud and one for mud that has passed through the drill bit, with subtraction of the former spectrum (or intensity at a single wavelength) from the latter spectrum (or intensity at a single wavelength), the difference being the spectrum (or intensity) of the species of interest. Note that the mud that has passed through the drill bit (the mud in the annulus) contains drill solids, particles of various sizes acquired as the result of drilling, ranging in diameter from a micron or two to centimeters. Unfortunately, total reflectance is well known to those knowledgeable in the art to be notoriously dependent on particle size in turbid fluids and to be difficult to quantify in the laboratory. Thus, a subtraction operation applied to two profiles that are not quantitative is highly unlikely to produce useful results.

The sol/gel approach is feasible for single-use measurements if the target species can be reacted in such a way as to produce a species with color that can be detected by the optical system. Of the mud contaminants listed in the various claims, the one most likely to be detected by a color-generating reaction is $H_2S$; for this reason, the remainder of the discussion will focus on that material. The method relies on diffusion of the target analyte through a porous glass medium to encounter a chemical species designed to react with it to produce a colored product. The system requires water-based mud for optimum reactivity since the glass is water-wet, and the reactions take place in an aqueous medium. Thus, this approach is highly unlikely to be useful with synthetic-/oil-based muds, which have hydrocarbons as the external phase. For water-based muds, the pH is typically at around 9 and is often higher, with the result that an incursion of a few, or even a few hundred, ppm of $H_2S$ is not considered a problem; detection at the surface is adequate. Operators concerned about the possibility of $H_2S$ typically raise the pH of their muds, add a buffer to provide extra pH protection, and/or add a sulfide scavenger, of which several are commercially available.

A key element of the sol/gel approach is that once a unit has reacted to produce a species detectable by optical spectroscopy, it cannot be re-used. Thus, the method cannot be used to evaluate mud chemistry downhole on a routine basis.

The authors of '323 claim that the detection methods include the use of "visible light, infrared, near infrared, ultraviolet, radio frequency, electromagnetic energy, and nuclear energy", however all are not demonstrated in the patent. Electromagnetic energy encompasses all of the preceding types in this list, and the patent provides no description of the use of nuclear energy. The authors only provide a description of a non-radioactive tagging atom, deuterium.

The use of micro-systems is known in art relating to, for example, biology, medicine, and explosives. Sandia National Laboratories (a DOE organization) has disclosed the use of micro-systems to detect a variety of products. This organization has investigated the use of micro-scale gas chromatography coupled with surface acoustic wave sensors to detect explosives, among other materials. Furthermore, they have developed a hand-held device involving micro-scale chromatography, with the specific application of the detection of explosives. Sandia has also developed two methods of chemical detection for application to explosives and weapons of mass destruction. An underwater unit, for explosives, utilizes an ion mobility spectrometer in identifying the chemical signatures of the materials. A vapor unit relies on acoustic wave sensors developed for specific compounds. It is important to note that these systems have only been applied to explosives, and that single-use units are not appropriate for flowing systems in which repeated measurements must be made. The concept of analyzing aerosol particles is patented by Sandia in U.S. Pat. No. 6,386,015: "Apparatus to collect, classify, concentrate, and characterize gas-borne particles."

Investigators at the University of Washington, Seattle, are developing continuously operating methods of measuring the concentrations of a variety of analytes, but the primary field of application is medical. See, for example, U.S. Pat. Nos. 5,716,852; 5,948,684; 5,972,710; 5,974,867; 5,932,100; 6,134,950 and 6,387,290.

U.S. Pat. No. 5,910,286 discloses a chemical sensor that relies on a "molecular fingerprint", in which a cavity created in a crosslinked polymer is exactly the size and shape of the target analyte. The focus of this approach is a single-use detection of a single chemical species. No specific application is described.

U.S. Pat. No. 5,984,023 discloses downhole in-situ measurement of physical or chemical properties of cores as they are being taken, including porosity, bulk density, mineralogy, and fluid saturation. The major focus is on rock properties, and the limited fluid analysis aspects of the patent are so general as not to be applicable to analysis of mud, completion fluid, or production fluid analysis.

U.S. Pat. No. 6,023,540 builds upon two earlier patents (U.S. Pat. Nos. 5,244,636 and 5,250,264) in describing the development of fiber optic bundles with multiple arrays of microspheres coated with specific materials that react with the target analyte to provide a unique signature. While no specific application or type of application was described for this tool, the approach is single-use and is not feasible for use in a flowing fluid.

U.S. Pat. No. 6,070,450 describes a gas sensor capable of detecting methane and carbon monoxide in a single device using a layer structure, in which the surface of a sensor for "city gas" (methane and the like) is overlain by a sensor for incompletely burned gases such as carbon monoxide. This device is designed for use as part of an alarm system and is single-use.

U.S. Pat. No. 5,822,473, which builds upon U.S. Pat. No. 5,760,479, describes the development of an integrated microchip chemical sensor designed to detect the presence of a single compound in a single-use application. Again, these single use systems would be unfit for flowing systems in which repeated measurements must be made.

U.S. Pat. Nos. 5, 610,708 and 5, 502,560 describe mechanics of measurement for a micro-scale grating light reflection spectroscopy probe for use as a process monitor. The application specifically described is particle size discrimination of dendrimeric particles in water solution.

The Center for Process Analytical Chemistry (CPAC) at the University of Washington (UW) sponsors NeSSI, the New Sampling/Sensor Initiative, to develop new miniature sampling systems based on semiconductor standards adapted to use in providing real-time feedback on the concentrations of multiple chemical species in process chemistry, but no patents regarding microfluidic testing or devices have been granted. The objective of the work is the development of methods of handling the information rather than the development of new sensors.

Other research abstracts from CPAC propose: 1) vapochromic detection and identification of volatile organic compounds applicable to a variety of simple compounds in a single-use approach; 2) surface plasmon resonance sensors, with proposed applications for bioanalytes; 3) Raman spectroscopy for process monitoring and materials characterization (Historically this approach has been limited to white solids or colorless solutions since the intense power of the laser is absorbed by darker-colored materials, resulting in rapid temperature increases. Application to drilling fluids, for example, would be limited on this account. And application to, for example, drilling fluids would be limited due to the complexity of the spectra and the insensitivity to metal ions); 4) Process liquid chromatography and sampling on a micro-scale are under development; and 5) The concept of a "Lab-on-a-Valve" for the monitoring of fermentation. No patents are known to have issued on any of these concepts in development.

APS Technology, Hellertown, Pa., has a DOE contract for a three year project for the development of a downhole sensor for production fluids, however it only contemplates a very gross evaluation of water, gas, and oil.

Microfluidics is a term for chemical analysis executed in microsized channels etched on a glass plate. An early patent for a microfluidic device is U.S. 5, 376,252, assigned to Pharmacia Biosensor. Microfluidic sensors and devices have been developed primarily for medical and biotechnology applications. Analyses such as, for example, DNA and RNA characterization have been carried out on small chips. For example, U.S. Pat. Nos. 6,358,387; 6,306,659; 6,274,337; 6,267,858; 6,150,180; 6,150,119; 6,132,685; 6,046,056; and 5,942,443, assigned to Caliper Technologies, Inc., disclose microfluidic devices and methods that are useful for performing high throughput screening assays. For an overview of microfluidics see Whitesides, G. M., Strock, A. D., [2001] "Flexible Methods for Microfluidics," *Physics Today*, 54 (6), 42–48.

There is a need in the art for a convenient method of continuous or intermittent measurement and analysis of drilling fluid chemicals. It would be particularly desirable if the method required only small amounts of sample and reagents and provided reliable, reproducible results. Deficiencies in the drilling fluid or the presence of influxes could be detected in real-time, potential well control or hazardous situations could be avoided, appropriate treatment could be applied, costly mud-related delays could be averted, and expensive production shut downs minimized. Such a system could more efficiently address drill fluid chemistry problems relating to drilling fluid flocculation and chemical imbalances and hazardous influxes of $H_2S$, $CO_2$, and $CH_4$. In addition, the method could also provide valuable measurements of hydrocarbon gases, noxious gases, crude oil, water, tracers, and inhibitor (scale and asphaltene deposition, hydrate formation) concentrations.

SUMMARY OF THE INVENTION

The method of the present invention allows automated chemical measurements on drilling-, drill-in, completion-, production-, and formation fluids using microfluidics that require only small quantities (i.e. microliters) of fluid and reagents to perform the tests, thus permitting minimal turn-around time, minimal sample size, minimal human and environmental impacts of chemicals due to the use of lowest effective concentrations. The present invention will also permit compatibility tests of treatment fluids with formation fluids, optimization of inhibitor concentrations, and improved drilling fluid management.

The present invention can be incorporated in an on-site benchtop tool, an in-line tool, or in a down-hole chemical analyzer.

In accordance with the foregoing, the present invention is a method for performing intermittent or continuous analysis of fluids used or produced in the process of drilling, completion and production of a well, comprising:

1) Collecting samples of fluids from the fluid stream;
2) Preparing samples;
3) Performing selected analytical tests on a fluid chemical analyzer using microfluidic methods;
4) Providing a means of detecting results of the tests and generating data;
5) Translating said data to provide results of said analytical test; and
6) Monitoring said results to adjust selected aspects of the drilling, drill-in, completion or production operation.

In further explanation of each step:
(1) The sample can be collected from the flow line to or from the well, near the drill bit, or at pre-determined sample collection points where the drilling-, drill-in-, completion-, formation-, or production fluid are flowing or stored. The fluid requirements are less than one cubic centimeter of sample fluid. It is desirable, but not required to filter the collected fluid through a filter (such as a hardened circular paper filter).

(2) The sample fluid has to be prepared to allow a useful measurement. This preparation may include, for example, sample dilution in order to reach a uniform viscosity of all the fluids (including fluorescent dyes, buffers and standard solution) or to reach a chemical concentration that is within the sensitivity of the fluorescent dye. Sample preparation may also include further filtration of the fluid.

(3) The microfluidic devices are glass- or polymer plates that have a pre-defined pattern of etched or printed or molded channels and wells on them. The receptacles or so-called wells on these plates hold the sample fluid, and, depending on the selected test, may also contain buffer solutions, fluorescent dyes, and liquid chemical solutions for chemical reactions or mixing of fluids. These channels or wells may be pre-treated to alter surface properties of the glass or polymer; they may contain typical micro-electric devices such as pumps, valves or heating elements. The transport of the fluid inside the channels is accomplished by using electro-kinetic forces (i.e. applying an electric field) or by applying a pressure gradient across the channels.

(4) A typical procedure may measure the concentration of a sample by comparison to a known standard fluid (for example by using fluorescent dyes and generating a standard and a measurement curve), or measure the resistivity of a fluid, the relative flow in a channel, compatibility of two or more fluids, or the viscosity of a fluid.

Measuring a concentration of a sample may be achieved by, for example, generating a standard curve by using a well-defined standard solution that contains a known concentration of the analyte. A suitable fluorescent dye is added to the standard solution and the quenching or increase of the dye's intensity by the analyte is measured using standard fluorescence detection methods (i.e. photomultiplier tubes). Additional in-situ dilutions may be performed. In the same or separate microfluidic protocol or on the same or separate plate the measurement curve is generated using the same suitable fluorescent dye. Additional in situ dilutions of the sample may be performed. By comparing the thus generated standard and sample curves the concentration of the sample can be determined.

(5) Converting the measured data to provide test results may be done singly by comparing the standard curve to the sample curve, by applying equations, or by automated computer routines. For example, measuring the resistance of a fluid may be achieved by using the following equations:

$$\text{Voltage} = \text{Resistance} * \text{Current} \qquad \text{Eq. 1}$$

$$\text{Resistance} = \frac{\text{specific electric resistance} * \text{length}}{\text{cross sectional area}}$$

(6) The monitoring of chemical properties allows the identification of imbalances in the fluid's chemistries, which may potentially affect the technical performance of the drilling-, drill-in, completion process, the environmental compliance of the aforementioned fluids or the production potential of the well. The concentration of certain chemicals may be adjusted, mitigating chemicals such as oxygen scavengers, corrosion inhibitors, biocides or scale, hydrate, or asphaltene precipitation inhibitors may be added in response to the timely measurement.

DETAILED DESCRIPTION OF THE INVENTION

The method of the present invention allows automated chemical measurements that require only small quantities (i.e. microliters) of fluid and reagents to perform these tests, thus permitting minimal turn-around time, minimal sample size, minimal human and environmental impacts of chemicals due to the use of lowest effective concentrations. The present invention will also permit compatibility tests of treatment fluids with formation fluids, optimization of inhibitor concentrations, and improved drilling fluid management.

The method of the present invention can be used to increase efficiencies of drilling operations by monitoring drilling fluid chemistries and presence and concentrations of ions, polymers, and inhibitors added for safety and performance reasons.

The method can be employed for tests that are currently used in routine analysis and also for tests that are considered too complex for routine measurements using the conventional methods of analysis.

Examples of tests that could employ microfluidic methods are measurement of concentrations such as: chloride content, polymer concentration, water hardness (calcium and/or magnesium ions), iron content, potassium content, silicate concentration, salinity, heavy metal concentration, concentration of amine-type shale inhibitors, presence of oxygen scavengers, production allocation by detecting trace elements, bromide ion, sulfides, thiosulfites, phosphates, biocides, and concentration of hydrate inhibitor. Examples of typical compatibility tests include: compatibility of formation fluid with the completion fluid, detection of crude oil and emulsions, measurement of shale reactivities, and compatibilities of completion acids and brines with formation fluids. Typical measurements to test the reactivity of shales are: methylene blue test, zeta potential, and effectiveness of polymers. Examples of other tests where microfluidics can be applied are: alkalinity, detection of enzymes, specific biopolymers, and pH.

In the procedure of the present invention fluid samples are taken, continuously or intermittently, from the flow stream for analysis. The location of the fluid samples may be, but is not limited to, the flow lines to the well and from the well, bottom hole assembly near the drill bit, under the cuttings shakers, and at a dedicated production line sample station.

The present invention can be incorporated in an on-site benchtop tool, an in-line tool, or in a down-hole chemical analyzer.

Fluid Chemical Analyzer:

The fluid chemical analyzer for testing fluids can be any kind of sensor, micro-system or means of analyzing in the art that is not limited to one use. The analyzing tool is preferably a microfluidic device made of glass- or polymer plate(s) that have a pre-defined pattern of two dimensional or three dimensional etched, molded or printed channels and wells in them. Typically, such channels or chambers will include at least one cross sectional dimension that is in the range of from about 0.1 $\mu$m to about 500 $\mu$m, and preferably from about 1 $\mu$m to about 100 $\mu$m. Dimensions may also range from about 5 $\mu$m to about 100 $\mu$m. Use of dimensions of this order allows the incorporation of a greater number of channels, chambers or sample wells in a small area, and utilizes smaller volumes of reagents, samples, and other fluids for performing the preparative or analytical manipulation of the sample that is desired. Such devices are discussed, for example, in U.S. Pat. Nos. 5,165,292 and 5,876,675, incorporated by reference herein in the entirety. The channels or wells may be pre-treated to alter surface properties of the glass- or polymer channels, and they may contain typical micro-electric devices such as pumps, valves or heating elements. The transport of the fluid inside the channels may be accomplished by using electro-kinetic forces (i.e. applying an electric field) or by applying a pressure gradient across the channels. Simple chemical reactions may be executed inside the channels. The types of measurements in such microfluidic devices may include the determination of sample concentrations, reactivity, relative flow, viscosity, hydraulic, or electric resistivity.

A suitable microfluidic device typically has at least three or more wells etched or cut into the plate with channels connecting the wells. These wells serve as reservoirs to hold the reagents such as, for example, the sample fluid, standard fluid, buffer for dilution, or fluorescent dye and a waste well. The wells are connected with the aforementioned channels such that mixing among these fluids can take place. For example, the well containing the sample fluid may be connected with a buffer well, a dye well, and the waste well. The fluids are moved through the channels by pumps or by electrokinetic forces. A photomultiplier may be directed to any point in the network of channels, but preferably to a section of the channel where all the mixing has taken place and the reaction of the sample or standard fluid to the dye can be observed.

Fluid Flow in Microfluidic Devices:

The microfluidic devices used herein to analyze fluids are characterized by the use of fluid transport and direction systems that either employ mechanical pumps or valves, as discussed for example in U.S. Pat. No. 6,171,067, incorporated by reference herein in the entirety, or the application of external pressure, or electro-kinetic flow to selectively move and direct the fluids through the various interconnected series of channels or chambers contained in the device or system. One example of controlled electroosmotic flow is described in published International Patent Application No. WO 96/04547 to Ramsey, which is incorporated herein by reference in its entirety. In brief, when an appropriate fluid is placed in a channel or other fluid conduit having functional groups present at the surface, those groups can ionize. For example, where the surface of the channel includes hydroxyl functional groups at the surface, i.e., as in the case of silica, protons can leave the surface of the channel and enter the fluid. Under such conditions, the surface will possess a net negative charge, whereas the fluid will possess an excess of protons or positive charge particularly localized near the interface between the channel surface and the fluid. By applying an electric field across the length of the channel, cations will flow toward the negative electrode. Movement of the positively charged species in the fluid pulls the solvent with them. The steady state velocity of this fluid movement in the channel is directly proportional to the zeta potential of the surface that is in contact with the fluid being moved. (Also see, for example, U.S. Pat. Nos. 5,304,487 and 5,800,690.)

Microfluidic Measurement:

An example of a typical procedure, in its basis not uniquely restricted to the well fluids, generates a standard and a measurement curve. The procedure, or measurement protocol, is preferably pre-determined and written into a simple software routine that controls the pumps or voltage or current applied across the channels or chambers. The test fluid, standard fluid, fluorescent dyes, and if required other reagents such as buffer fluids are introduced into the receptacles or wells on the microfluidic plates. The introduction of small volumes of test compounds can be accomplished manually, using a standard pipette, or automatically using, for example, an electropipettor, as discussed in U.S. Pat. No. 5,779,868, incorporated by reference herein in the entirety. These receptacles or chambers typically need less than 25 microliters of the fluids.

The standard curve is generated by using a well-defined standard solution that contains a known concentration of the analyte. A suitable fluorescent dye (the intensity of which is increased or decreased by the presence of the analyte in question) is added to the standard solution. The fluorescent dye is excited by a suitable light source such as, for example, a mercury lamp, argon lamp, xenon lamp, LED lamp, or specific laser. A set of excitation, emission and dichroic mirrors is chosen such that the fluorescent excitation and emission wavelengths are optimized. Bandwidth filters may be employed to optimize excitation and emission spectra.

The quenching or enhancement of the dye's intensity by the analyte is measured using standard fluorescence detection methods (i.e. photomultiplier tubes). Additional in situ dilutions may be performed. The fluorescent intensity is recorded. In the same microfluidic plate the measurement curve is generated using the same suitable fluorescent dye. Additional in situ dilutions of the sample may be performed. The fluorescent intensity of the dye is measured and recorded. By comparing the thus generated standard and sample curves the concentration of the sample can be determined.

The microfluidic device may be incorporated in a benchtop instrument, which provides for microfluidic applications and may include a microfluidic device with wells and channels, an excitation source, suitable filters and photomultipliers and a storage device for the test results. The instrument design may allow for the use of methods for illumination and detection including broad-spectrum lamps such as, for example, mercury, argon, or more narrow lamps such as LED of a pre-determined bandwidth. An analyte detector may be mounted proximal to the substrate-viewing region to detect formation of products and/or passage of reactants along a portion of the substrate. A computer may be operably linked to the analyte detector, to monitor formation of reactants, and the like. See U.S. Pat. No. 6,046,056.

In the method of the present invention the steps described can be utilized to obtain a number of key measurements. Following are tests that can be performed on drilling-, drill-in, completion-, formation and production fluids in real-time, on-site or remote, faster, more reliably, and more economically, with better reproducibility of results:

Shale reactivities and zeta potential can be measured using dyes such as polymethine dyes, including, but not limited to styryl dyes, oxanols, cyanines, particularly carbocyanines, and merocyanine 540. Other suitable dyes include sulfur compounds, including, but not limited to rhodamine.

Ion concentrations much higher than would be observed in biological systems can be measured using low affinity indicators, or diluting the sample sufficiently to move the ion concentration in the sample into the range of higher-affinity dyes. Suitable examples are calcium indicators, including, but not limited to BTC, Mag-Fura-2, Mag-Fura-5, and Mag-Indo-1, (described in U.S. Pat. No. 5,501,980) available from Molecular Probes.

Calcium concentration can be measured using, for example, a dye that increases in intensity upon addition of calcium, such as fluo-5N (U.S. Pat. No. 5,049,673) or alternatively Oregon Green (BAPTA-2 octapotassium salt, available from Molecular Probes).

Amine-type shale inhibitors can be measured using dyes that bind to the amine groups of proteins, and enzymes can be detected using dyes that are protein specific or that bind to amines. These measurements may be used for quality assurance during completions. Suitable dyes for these tests include, for example, the carboxy-fluorescein derivative series, including, but not limited to Alexa dyes, one example of which is Alexa Fluor® available from Molecular Probes.

Biopolymers in the fluid can be detected by reacting them with species-specific enzymes and then detecting glucose, an end product of enzymatic activity. Suitable substrates include dihydrofluoresceins (also known as fluorescing) dyhydrorhodamines, and 10-acetyl-3,7-dyhydroxyphenoxazine, sold under the trademark Amplex®Red. (U.S. Pat. No. 6,265,179)

Oxygen scavengers can be measured. This test will be particularly useful in high temperature wells for increasing the effectiveness of polymers in water-based muds. Suitable dyes include those used for measuring reactive oxygen species, including, for example, but not limited to Luminol and dyes in the acridine group, such as, Lucigenin.

Crude oil and emulsions can be detected using lipid-sensitive dyes selected from hydrophobic dyes, including but not limited to Nile Red. The amount of water in invert mud systems can be measured using flow-tracing dyes. Suitable dyes include, but are not limited to fluorescein. Information on production allocation can be obtained by measuring trace elements such as sulfur, nickel, and vanadium using appropriate dyes.

Water hardness can be estimated as total calcium and magnesium. Suitable dyes include fluorescent $Ca^{+2}$ indicators excited with UV light or visible light. Examples include, but are not limited to, Rhod-2 related derivatives and Calcium Green indicators, as well as the halide-specific fluorescent dye, 6-methoxy-N-(3-sulfopropyl)quinolinium (SPQ), and the like. Bromide ion (tracer in flowback systems) can be measured by conversion to hypobromite ion and reaction with dyes of the type including, but not limited to, Rhodamine 6G Heavy metals, including zinc, barium, and cadmium, can be measured using a fluorescent transition metal indicator, such as, for example, Phen-Green, or a zinc chelator and heavy metal indicator such as 5-nitrobenzothiazole coumarin (BTC 5N). Very high chloride concentrations in excess of biological levels can be measured using, for example, Acridine Orange, one of the acridine series of dyes.

A pH above 8 or less than 5 can be determined using pH indicators, including but not limited to SNARF-1 and BCECF. Levels of sodium and potassium can be measured using, for example, Sodium Green, SBFI, and PBFI, (benzofuranyl fluorophores linked to a crown ether), all available from Molecular Probes. Sulfides can be detected using, for example, the chromogenic papain substrate, L-BAPNA (α-N-benzoyl-L-arginine 4-nitroanilide). Bimane derivatives, such as, for example, monobromobimane, available from Calbiochem®, can be utilized for detection of sulfides, $H_2S$ which is very toxic, and thiosulfate, which is used as a corrosion inhibitor in packer fluids.

Inorganic phosphates can be detected utilizing phosphate assay kits, such as PiPer Phosphate and EnzChek®, available from Molecular Probes. The detection of microbes in order to optimize the concentrations of biocides can be accomplished using a cell permeant dye, such as MitoTracker®, available from Molecular Probes. In order to determine the efficiency of biocides in water-based muds, ethidium homodimer and dihydroethidium can be employed for staining dead and live cells. The measurement of iron content is useful for optimizing the concentrations of $H_2S$ scavengers and also the extent of corrosion and can be accomplished using calcein. Compatibilities of completion acids and brines with crude oils (including asphaltene precipitation) can be determined by measuring relative flow changes in microfluidic channels.

Compatibilities of formation brine with completion fluid can be determined by measuring relative flow changes in microfluidic channels.

Data for use in production allocation can be obtained by measuring hydrocarbon species by liquid chromatography.

Resistivity or viscosity can measure hydrate inhibitors, such as ethylene glycol and methanol.

Buffers are used to maintain pH during reactions. The type of buffer is dependent on the pH range required for the particular use and on the detailed chemistry of the dye. Some dyes can handle high pH, and borate or carbonate buffers (pH about 9) would be suitable, whereas some other dyes require lower pH and buffers such as TRIS or MOPS or even phosphate (pH around 7–7.5) are more appropriate. Other dyes might require still lower pH values and would require different buffers. In Examples 1 & 2 the buffer employed to demonstrate the method was 10 mM Tris pH 7.5.

The invention is useful for a number of different tests of formation fluids and production fluids, as discussed above, however the examples herein present analysis of measurements of production fluid for resistivity and chloride concentration. Resistivity of the drilling fluid filtrate was measured in Example 1. Where saltwater/PHPA filtrate is analyzed it is preferred to dilute the solution. A suitable range for dilution is in the range of 1:1 up to 1:100, preferably 1:10. Freshwater/PHPA filtrate was analyzed undiluted.

Fluorescence was measured in Example 2. A commercially available fluorescent dye, Lucigenin, was used to test chloride concentrations in Example 2 and provided desirable results. Lucigenin is generally a useful Cl⁻ indicator in liposomes and reconstituted membrane vesicles and was suitable.

In some measurements, such as resistivity, the samples are exposed to an electric current.

In samples where the measurement principle is fluorescence, the samples are excited with a wavelength in the range of 360 to 700 nm. The wavelength is determined by the excitation spectrum of the fluorescent dye in use. For example, the preferred excitation wavelengths for lucigenin, a chloride-sensitive dye are 368 nm and 455 nm.

The following examples will serve to illustrate the invention disclosed herein. The examples are intended only as a means of illustration and should not be construed as limiting the scope of the invention in any way. Those skilled in the art will recognize many variations that may be made without departing from the spirit of the disclosed invention.

Experimental

Studies were conducted measuring the total resistivity and chloride concentration of two drilling fluid filtrates using microfluidic devices. Standard curves were successfully generated that were translated into total resistivity and chloride concentrations of the fluids. This study also showed that several issues like accurate calibration curves of the standard fluids, measurement protocol and choice of fluorescent agent are important to generate reliable results.

The chips used in the examples are standard, versatile chips useful for chemical assay, available from microfluidics suppliers like Caliper Technologies, Aclara, and Micronics.

In addition to the chip manipulations and chemical composition, software programs were employed for controlling the flow rates, dilutions, and measurements during the experiment.

The fluids tested were standard solutions of sodium chloride and drilling fluid filtrate. The drilling fluid composition is shown in Table 1. The drilling fluid was prepared and hot rolled at 150° F. for 16 hours. The fluid was filtered in a standard API fluid loss cell using hardened filterpaper (FANN) for 3 hours, collecting several cubic centimeters of filtrate.

TABLE 1

Drilling fluid composition: unweighted NaCl/PHPA mud

|  | NaCl/PHPA | Freshwater/PHPA |
|---|---|---|
| Water (deionized) [bbl] | 0.91 | 0.91 |
| Bentonite [ppb] | 8.00 | 8.00 |
| NaOH [ppb] | 0.10 | 0.10 |
| NaCl [ppb] | 39.50 | — |
| Fluid loss control agent I [ppb] | 1.00 | 1.00 |
| Fluid loss control agent II [ppb] | 1.50 | 1.50 |
| PHPA | 1.0 | 1.0 |
| Xanthan gum | 0.50 | 0.50 |

EXAMPLE 1

In Example 1, resistivity or conductance of freshwater/PHPA drilling fluid filtrate and of sodium chloride/PHPA was measured. The fluid was 2M NaCl in a buffer, 10 mM Tris pH 7.5. The stock solution was diluted with water to working solutions of 50 mM, 100 mM, 250 mM, and 500 mM. The freshwater/PHPA filtrate was used undiluted, while the saltwater/PHPA filtrate was diluted 1:10.

The microfluidic device that was employed for measuring the resisitvity used at least three wells to hold the fluids: sample fluid, standard fluid and waste well. The wells were connected to each other and all to the waste well.

Before use the chip was cleaned with a 1 Normal NaOH solution, and flushed with buffer before introducing the sample and the standard fluids. A voltage of 100V, 200V, 300V and 400 V was applied across the channels and the responding current was measured, thus calculation of the resistance was possible using aforementioned Equation 1. A software program was employed to evaluate conductance.

Figure 1:
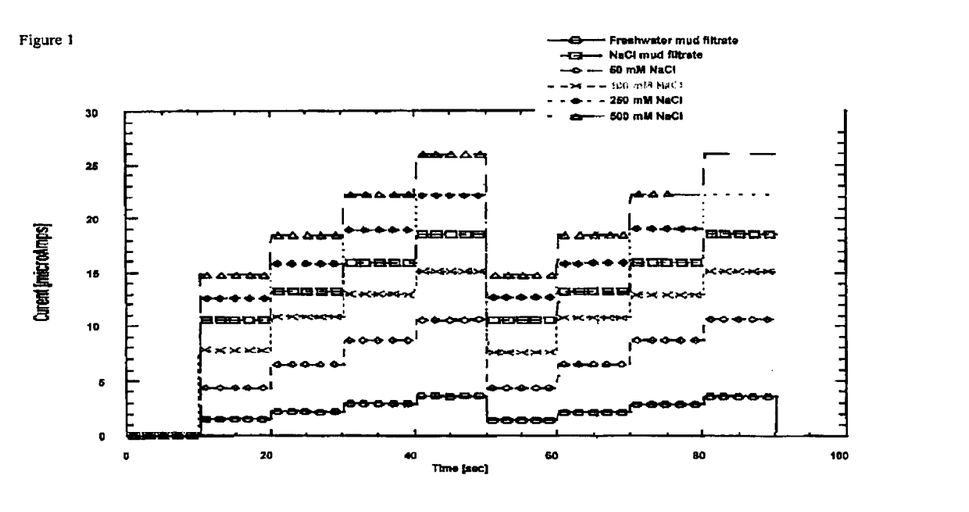
FIG. 1 is a graph showing the original stair-step response in the resistivity measurement of standard solutions and drilling fluid filtrates.
Figure 2:
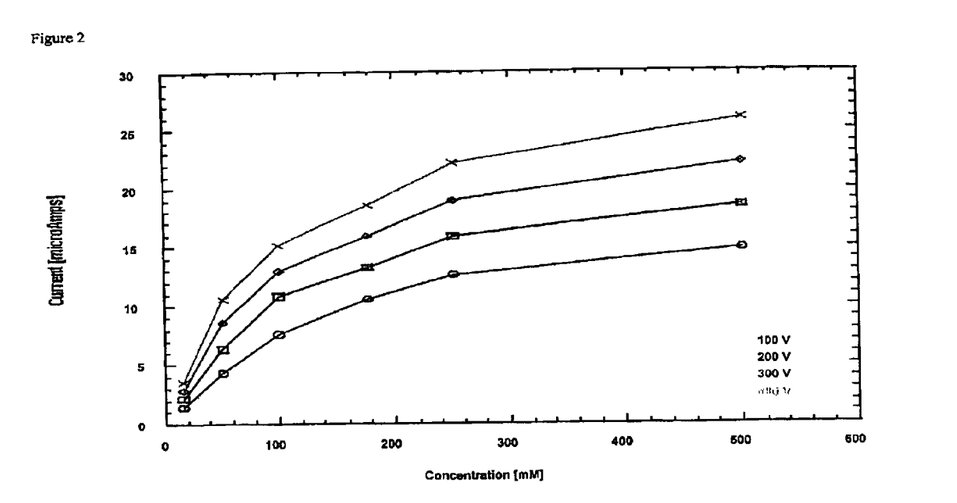
FIG. 2 is a time-averaged graph showing resistivity measurement of standard solutions and drilling fluid filtrates.

The raw results of the resistivity measurement of freshwater/PHPA drilling fluid filtrate, sodium chloride/PHPA and standard solutions are shown in FIGS. 1 and 2.

FIG. 1 shows the stair-step response when the voltage is increased from 100 to 400 Volt. Each experiment is repeated once. The quality of the measurement signal is very good, with little noise.

When the data are re-plotted with current as a function of the equivalent sodium chloride concentration (note that although sodium chloride is the dominant ion contributor in the filtrate, some ions come from the ionic polymers and the bentonite in the drilling fluid). The response is clearly non-linear (FIG. 2): a steep initial increase followed by an asymptotic approach to a limiting value of current.

Based on the drilling fluid composition (mass of sodium chloride in the fluid), the calculated molar concentration of the fluid is 186.8 mM. The average measured molar concentration is 176.6 mM. The measured average concentration of the freshwater sample is 16.7 mM. A summary of the results is shown in Table 2.

TABLE 2

Average measured concentration of the drilling fluid filtrates based on resistivity measurements

| Average 2 runs | Freshwater/PHPA [mM] | NaCl/PHPA [mM] |
|---|---|---|
| 10–20 sec | 16.8798 | 188.0051 |
| 20–30 sec | 16.65734 | 172.5479 |
| 30–40 sec | 16.52543 | 172.8534 |
| 40–50 sec | 16.82557 | 173.0319 |
| Average concentration [mM] | 16.72204 | 176.6096 |

EXAMPLE 2

In Example 2 chloride concentration was measured. The measurement principle in this experiment is fluorescence. The microfluidic device that was employed for measuring the chloride concentration used at least five wells to hold the fluids: sample fluid, standard fluid, buffer, dye and waste well. The wells were connected to each other and all to the waste well. The standard stock was 100 mM NaCl in a buffer, 10 mM borate buffer pH 9.2. The working solution was 100 mM diluted with 10 mM borate buffer pH 9.2. The dye was 40 µM Lucigenin in 10 mM borate buffer pH 9.2. The samples were freshwater and 10% NaCl drilling fluid. The freshwater sample was used undiluted, while the NaCl-containing drilling fluid filtrate was diluted 1:17. The protocol is as follows:

(1) Cleaning the chip with 1 Normal NaOH solution and flushing the chip with HPLC grade water.

Figure 3:
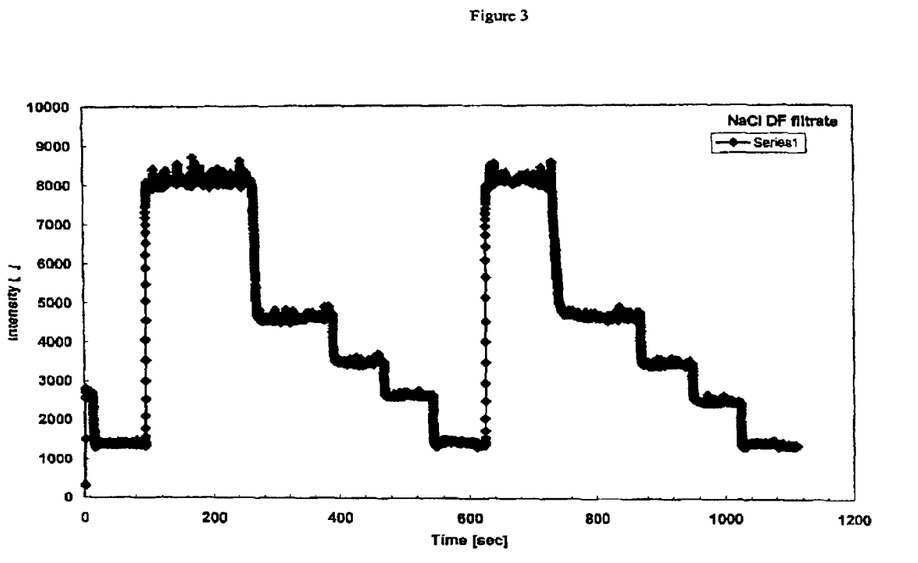
FIG. 3 is a graph showing the fluorescent intensity of a NaCl-containing drilling fluid filtrate. The fluorescent dye is quenched by the presence of chloride in the filtrate.
Figure 4:
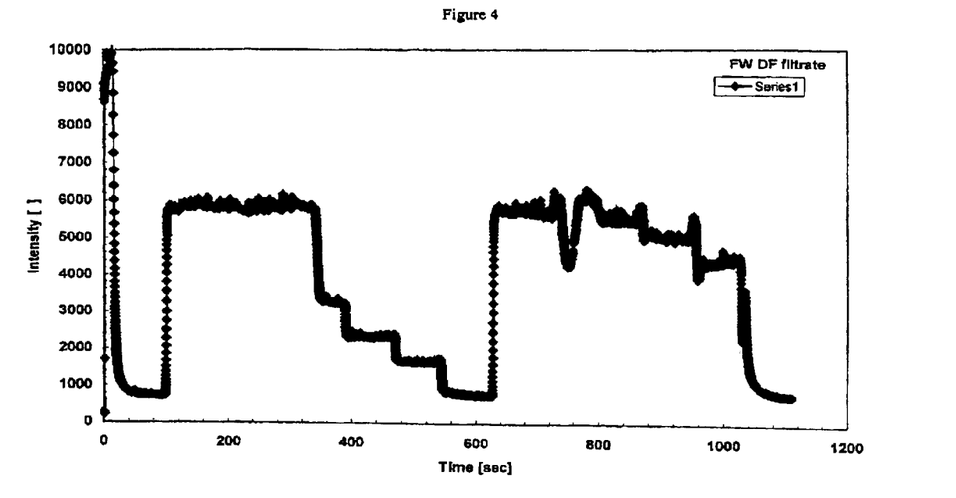
FIG. 4 is a graph showing the fluorescent intensity of a freshwater-containing drilling fluid filtrate. The fluorescent dye is quenched by the presence of chloride.

(2) Then the water was removed from the wells and the wells loaded with the sample, standard, buffer, and dye. A software program was employed to control flow rates, dilutions, and measurements during the experiment. It also provided the standard curve and sample curve. The program provided for measuring the fluorescence of the unquenched dye as well as dye quenched with three concentrations of chloride. The software allowed the dilution on the chip. As a first step a "baseline" was created by flowing 100% buffer solution past the detection point and measuring the background intensity. In the second step 100% dye flowed past the detection point to measure the maximum intensity. The subsequent steps measure the quenching (i.e. diminishing intensity) of the dye in the presence of chloride ions. The dilution steps that can be seen in FIG. 3 are: 1:16; 1:8; 1:4 for the NaCl-containing filtrate. The dilution steps that can be seen in FIG. 4 are 1:8; 1:4; 1:2 for the freshwater drilling fluid filtrate.

Results: The raw results of the chloride measurements are shown in FIGS. 3 and 4 for the freshwater and 10% NaCl drilling fluid filtrate, respectively. The base line and the 100% dye line are shown in the first two steps of the curve on FIGS. 3 and 4. Since Lucigenin is a quenching dye, any addition of chloride in the sample solution will be reflected in a decrease of the intensity of the dye. After the base line and 100% dye-line are established, the fluorescent dye (Lucigenin) is added to a standard solution, the fluorescent intensity is measured, the stair-step curve is generated by some additional points in the measurement representing 1:16, 1:8; and 1:4 (NaCl containing filtrate), and 1:8, 1:4 and 1:2 (freshwater containing filtrate sample) dilutions of the sample with the buffer. Then dye is added to the filtrate sample and the fluorescence intensity is measured. The fluorescence of this dye is quenched by the presence of chloride ion, resulting in a decrease in intensity of the fluorescence. In FIG. 3, the calibration of the standard and the measurement of the filtrate sample is shown by the two sets of cascading steps. In the first step of each set, the instrument is monitoring the fluorescence of the dye in the absence of any chloride.

A summary of the results of the chloride concentration tests is shown in Table 3. The calculated results for the 10% NaCl solution are in remarkably good agreement with the actual values.

TABLE 3

Average measured concentration of the drilling fluid filtrates based on fluorescence measurements

| Dilution | Standard concentration [mM] | Sample concentration in chip [mM] | Actual concentration (from NaCl in mud formulation) |
|---|---|---|---|
| 1:1 | 50 | 48 | |
| 1:3 | 25 | 22 | |
| 1:7 | 12.5 | 12.3 | |
| 1:1 | 50 | 49.5 | 46.5 |
| 1:3 | 25 | 28.5 | 23.25 |
| 1:7 | 12.5 | 17.5 | 11.63 |

EXAMPLE 3

Figure 5:
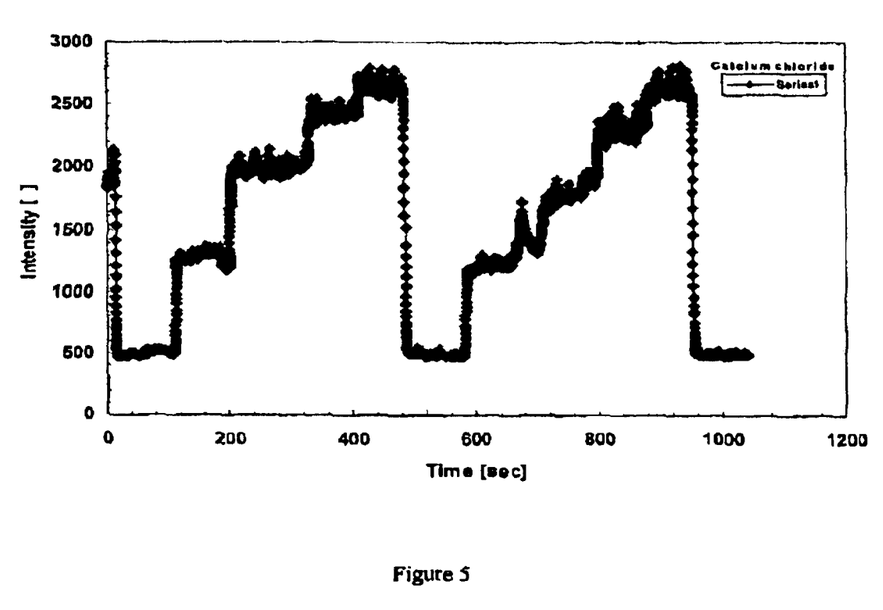
FIG. 5 is a graph showing the measurement of calcium concentration.

The third example shows the measurement of calcium concentration in a microfluidic chip. The measurement principle, again, is fluorescence, but here a fluorescent dye, fluo-5N (U.S. Pat. No. 5,049,673) is used. This dye increases its intensity upon addition of calcium. Note a similar response can be achieved using Oregon Green (BAPTA-2 octapotassium salt, patented and available from Molecular Probes). The sample preparation is as follows: five micromolar of Fluo-5N is diluted in a MOPS buffer. The starting concentration of calcium in the standard solution is 60 mM. The result is shown in FIG. 5. The first two steps of the stair steps are the buffer-base line and the 100% dye line the subsequent steps are of 1:16; 1:8 and 1:4 addition of the 60 mM calcium-buffer solution. The second stair step, using buffer solution and a 60 mM calcium solution (representing the test fluid) in separate wells is an identical stair case to the first staircase.

We claim:

1. A method for chemical analysis of fluids utilized or produced in hydrocarbon exploration and production industry, including, drilling, drill in, completion, formation and production fluids, which may be employed at rig site or in a remote location, comprising:
   a) Collecting samples of fluids from predetermined fluid collection points where the drilling-, drill-in-, completion-, formation-, or production fluid are flowing or stored;
   b) Introducing said samples into a microfluidic system for chemical measurement containing at least one microfluidic device characterized by at least one microfluidic channel and at least three reservoirs, optionally said microfluidic device operably connected to a computing device;
   c) Executing one or more selected tests on said microfluidic device;
   d) Providing a means of detecting results of the tests and generating data;
   e) Translating said data to provide results of said analytical test; and
   f) Monitoring said results to adjust selected aspects of the drilling, completion, and production operations.

2. The method of claim 1 further comprising the samples are collected from a position selected from flow lines to the well, flow lines from the well, bottom hole assembly near the drill bit, under the cuttings shakers, and at a dedicated production line sample station.

3. The method of claim 1 further comprising fluids are transported on the microfluidic device by a method selected from electro-kinetic forces (i.e. applying an electric field), by applying a pressure gradient across the channels, or by use of micro-electric pumps.

4. The method of claim 3 further comprising pressure, vacuum, voltage, or currents can be applied at all ports on the chip, in various combinations to provide maximum flexibility for the movement, addition, mixing, dilution and separation of fluids.

5. The method of claim 4 further comprising a computer software program is used to control flow rates, dilutions, and measurements.

6. The method of claim 1 further comprising the selected test utilizes fluorescence method.

7. The method of claim 6 further comprising:
   a) Generating a standard curve using a standard solution that contains a known concentration of the sample;
   b) Adding a suitable fluorescent dye to the standard solution;
   c) Measuring quenching or increase of dye's intensity using standard fluorescence detection methods, incorporating the use of photomultiplier tubes, and generating a curve;
   d) Comparing said generated standard and sample curves; and
   e) Determining the concentration of the sample.

8. The method of claim 7 further comprising employing bandwidth filters that optimize excitation and emission spectra.

9. The method of claim 7 wherein the concentration is determined by a method selected from visual comparison of the standard curve to the sample curve or by using automated evaluation of the concentration.

10. The method of claim 7 wherein all steps are incorporated in a computer program.

11. The method of claim 7 further comprising the selected tests selected from a test to measure shale reactivity and zeta potential.

12. The method of claim 11 wherein the dye is selected from styryl dyes, oxanols, carbocyanines, and rhodamine.

13. The method of claim 7 further comprising the selected test measures high ion concentration.

14. The method of claim 13 wherein the dye is an affinity indicator for high ion concentrations.

15. The method of claim 7 further comprising the selected test measures amine-type shale inhibitors and enzymes.

16. The method of claim 15 further comprising the dye is a protein specific dye capable of binding amines.

17. The method of claim 7 further comprising the selected test measures the presence of biopolymers.

18. The method of claim 17 further comprising the dye detects biopolymers by reacting them with species specific enzymes and detecting glucose.

19. The method of claim 7 further comprising the selected test measures the presence of oxygen scavangers using a dye for measuring reactive oxygen species.

20. The method of claim 7 further comprising the selected test detects crude oil and emulsions using lipid sensitive dyes.

21. The method of claim 7 further comprising the selected test measures water in invert mud systems using flow-tracing dyes.

22. The method of claim 7 further comprising the selected test measures trace elements selected from sulfur, nickel, and vanadium.

23. The method of claim 7 further comprising the selected test measures water hardness as a function of total calcium and magnesium.

24. The method of claim 23 further comprising the test utilizes fluorescent $Ca^{+2}$ indicators.

25. The method of claim 7 further comprising the selected test measures bromide ion by conversion to hypobromite.

26. The method of claim 7 further comprising the selected test measures heavy metals (Zn, Ba; Cd).

27. The method of claim 26 further comprising the test utilizes a dye selected from a fluorescent transition metal indicator, a zinc chelator, and heavy metal indicator.

28. The method of claim 7 further comprising the selected test measures chloride concentrations.

29. The method of claim 28 further comprising the test utilizes Acridine Orange.

30. The method of claim 7 further comprising the selected test measures sodium and potassium.

31. The method of claim 7 further comprising the selected test detects/measures sulfide.

32. The method of claim 7 further comprising the selected test detects/measures sulfides compounds.

33. The method of claim 7 further comprising the selected test is an assay for phosphates.

34. The method of claim 7 further comprising the selected test detects microbes.

35. The method of claim 7 further comprising the selected test determines the efficiency of blocides by detecting live and dead cells by staining.

36. The method of claim 7 further comprising the selected test measures iron content.

37. The method of claim 1 further comprising the selected test measures compatibilities of completion acids and brines with crude oil by measuring relative flow changes in microfluidic channels.

38. The method of claim 1 further comprising the selected test measures compatibilities of formation brines with completion fluid by measuring relative flow changes in microfluidic channels.

39. The method of claim 1 further comprising the selected test measures hydrocarbon species by liquid chromatography.

40. The method of claim 1 wherein the selected test is measurement of resistivity.

41. The method of claim 40 further comprising:
a) Exciting said sample with a current;
b) Plotting current as a function of equivalent concentration for sample at a given current; and
c) Calculating the molar concentration of the fluid using the following:

$$\text{Voltage} = \text{Resistance} \times \text{Current}$$

$$\text{Resistance} = \frac{\text{Specific Electrical Resistance} \times \text{length}}{\text{Cross Sectional Area}}.$$

42. The method of claim 41 wherein the current is in the range of 100 to 400 volts.

43. The method of claim 42 further comprising resistivity is used to measure hydrate inhibitors.

44. The method of claim 43 wherein the hydrate inhibitor is selected from ethylene glycol and methanol.

45. The method of claim 1 further comprising the microfluidic system is incorporated in a benchtop instrument at rig site.

46. The method of claim 45 further comprising the bench top instrument incorporates broad-spectrum lamps.

47. The method of claim 46 wherein the broad-spectrum lamp is selected from mercury or argon.

* * * * *